United States Patent [19]

Wehner et al.

[11] Patent Number: 5,272,192

[45] Date of Patent: Dec. 21, 1993

[54] MELAMINE DERIVATIVES AS STABILIZERS FOR CHLORIDE-CONTAINING POLYMERS

[75] Inventors: Wolfgang Wehner, Zwingenberg; Hans-Günter Köstler, Heppenheim/Bergstrasse, both of Fed. Rep. of Germany

[73] Assignee: Ciba-Geigy Corporation, Ardsley, N.Y.

[21] Appl. No.: 867,090

[22] Filed: Apr. 13, 1992

Related U.S. Application Data

[63] Continuation of Ser. No. 638,250, Jan. 4, 1991, abandoned.

[30] Foreign Application Priority Data

Jan. 9, 1990 [CH] Switzerland ............... 56/90

[51] Int. Cl.$^5$ .................. C08K 5/3492; C08K 5/09
[52] U.S. Cl. ...................... 524/87; 524/100; 524/399; 524/400
[58] Field of Search .............. 524/100, 396, 400, 399, 524/87

[56] References Cited

U.S. PATENT DOCUMENTS

| | | | |
|---|---|---|---|
| 3,084,135 | 4/1963 | Scullin | 524/100 |
| 3,496,136 | 2/1970 | Susi et al. | 524/100 |
| 4,312,988 | 1/1982 | Jacobs, III et al. | 544/196 |
| 4,786,672 | 11/1988 | Wehner | 524/100 |
| 4,992,494 | 2/1991 | Odaira et al. | 524/399 |

FOREIGN PATENT DOCUMENTS

| | | |
|---|---|---|
| 3037755 | 4/1978 | Japan. |
| 54-6043 | 1/1979 | Japan. |
| 56-43342 | 4/1981 | Japan. |
| 61-116512 | 6/1986 | Japan. |

OTHER PUBLICATIONS

D. F. Walker, et al. J. Am. Pharm. Ass. 39, 393 (1950).
D. W. Kaiser, et al. J. Am. Chem. Soc. 73, 2984 (1951).
D. E. O'Brien et al., J. Med. Chem. 6, 467 (1963).
Smolin, et al., "s-Triazines & Derivatives-The Chemistry of Heterocyclic Compounds" Chap. VI 309-388 (1967).
A. B. Borkovec et al., J. Med. Chem. 10, 457 (1967).

Primary Examiner—Paul R. Michl
Assistant Examiner—Tae H. Yoon
Attorney, Agent, or Firm—Luther A. R. Hall; William A. Teoli, Jr.

[57] ABSTRACT

Compositions containing
a) a chlorine-containing polymer,
b) 0.01 to 1% by weight, relative to the chlorine-containing polymer, of a compound of the formula I and/or its hydrochloride,

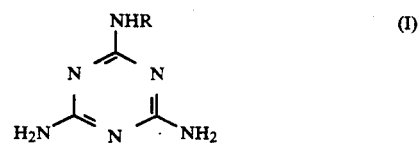

in which R is $C_6$–$C_{20}$alkyl, $C_3$–$C_{20}$alkyl interrupted by 1 to 5 oxygen atoms, $C_1$–$C_{20}$alkyl substituted by 1 to 5 OH, $C_3$–$C_{20}$alkenyl, $C_3$–$C_8$cycloalkyl, $C_1$–$C_4$alkyl-substituted $C_3$–$C_8$cycloalkyl, $C_7$–$C_{11}$phenylalkyl, $C_7$–$C_{11}$phenylalkyl which is substituted on the phenyl by 1 to 3 radicals, these radicals, independently of one another, being hydroxyl, chlorine, $C_1$–$C_4$alkyl, methoxy or ethoxy, or R is furthermore a group of the formula IIa or IIb,

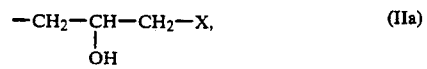

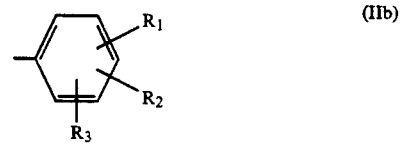

in which X is $C_1$–$C_{20}$alkyloxy, $C_1$–$C_{20}$alkylthio, phenyloxy, phenylthio, benzyloxy or benzylthio, and $R_1$, $R_2$ and $R_3$, independently of one another, are hydrogen, $C_1$–$C_{20}$alkyl, $C_1$–$C_{20}$alkyloxy, $C_1$–$C_{20}$alkythio, $C_2$–$C_{12}$alkyloxycarbonyl, $C_2$–$C_{12}$alkanoyl, phenyl, phenyloxy, phenylthio, hydroxyl, mercapto or chlorine, and c) 0.01 to 5% by weight, relative to the chlorine-containing polymer, of an Me(II) carboxylate and/or Me(II)-phenolate, in which Me(II) is Ba, Ca, Mg, Cd or Zn.

Some of the compounds of the formula I are novel.

13 Claims, No Drawings

MELAMINE DERIVATIVES AS STABILIZERS FOR CHLORIDE-CONTAINING POLYMERS

This application is a continuation, of application Ser. No. 638,250, filed Jan. 4, 1991, now abandoned.

The present invention relates to compositions containing a) a chlorine-containing polymer, b) a melamine derivative and c) a metal salt, to the use of a mixture comprising components b) and c) for stabilising a chlorine-containing polymer against thermal degradation and to novel melamine derivatives.

It is known that chlorine-containing polymers have to be protected against the damaging effect of light and heat, in particular during the processing to give moulded articles. A few melamine derivatives and their use as stabilisers for chlorine-containing polymers are described, for example, in JP-A-Sho 56/43,342, U.S. Pat. No. 3,084,135 and U.S. Pat. No. 3,496,136. The preparation of various melamine derivatives has already been described by D. F. Walker et al.; "J. Am. Pharm. Ass. 39, 393-396", 1951 by D. W. Kaiser et al.; "J. Am. Chem. Soc. 73, 2984-2986", 1963, by D. E. O'Brien et al.; "J. Med. Chem. 6, 467-471", 1967 by Smolin et al.; "s-Triazines and Derivatives—The Chemistry of Heterocyclic Compounds, Chapter VI, pp. 309-388" and also in 1967 by A. B. Borkovec et al.; "J. Med. Chem. 10, 457-461" and in U.S. Pat. No. 4,312,988. Melamine derivatives as odour-binding agents for polyvinyl chloride films are known from JP-A 79/6043 and JP-A 86/116,512.

The present invention relates to compositions containing
a) a chlorine-containing polymer,
b) 0.01 to 1% by weight, relative to the chlorine-containing polymer, of a compound of the formula I and/or its hydrochloride,

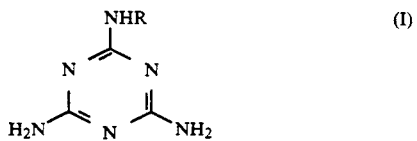

in which R is $C_6$-$C_{20}$alkyl, $C_3$-$C_{20}$alkyl interrupted by 1 to 5 oxygen atoms, $C_1$-$C_{20}$alkyl substituted by 1 to 5 OH, $C_3$-$C_{20}$alkenyl, $C_3$-$C_8$cycloalkyl, $C_1$-$C_4$alkyl-substituted $C_3$-$C_8$cycloalkyl, $C_7$-$C_{11}$phenylalkyl, $C_7$-$C_{11}$phenylalkyl which is substituted on the phenyl by 1 to 3 radicals, these radicals, independently of one another, being hydroxyl, chlorine, $C_1$-$C_4$alkyl, methoxy or ethoxy, or R is furthermore a group of the formula IIa or IIb, $$-CH_2-CH(OH)-CH_2-X, \quad (IIa)$$

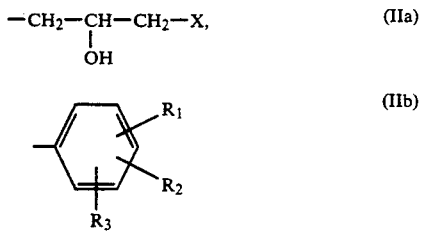

in which X is $C_1$-$C_{20}$alkyloxy, $C_1$-$C_{20}$alkylthio, phenyloxy, phenylthio, benzyloxy or benzylthio, and $R_1$, $R_2$ and $R_3$, independently of one another, are hydrogen, $C_1$-$C_{20}$alkyl, $C_1$-$C_{20}$alkyloxy, $C_1$-$C_{20}$alkylthio, $C_2$-$C_{12}$alkyloxycarbonyl, $C_2$-$C_{12}$alkanoyl, phenyl, phenyloxy, phenylthio, hydroxyl, mercapto or chlorine, and
c) 0.01 to 5% by weight, relative to the chlorine-containing polymer, of an Me(II) carboxylate and/or Me(II)-phenolate, in which Me(II) is Ba, Ca, Mg, Cd or Zn.

Component c) is preferably a mixture of Ba/Zn carboxylates if component b) is phenyl-melamine.

Examples of R as $C_6$-$C_{20}$alkyl are hexyl, heptyl, octyl, nonyl, decyl, undecyl, dodecyl, tridecyl, tetradecyl, pentadecyl, hexadecyl, heptadecyl, octadecyl, nonadecyl or eicosyl.

R as $C_3$-$C_{20}$alkyl which is interrupted by 1 to 5 oxygen atoms is preferably a group of the formula

in which r is 2 or 3, s is 1, 2, 3, 4 or 5, and Z is, for example, methyl, ethyl, propyl or butyl.

Examples of R as $C_1$-$C_{20}$alkyl which is substituted by 1 to 5 OH are hydroxymethyl, 2-hydroxyethyl, 3-hydroxypropyl, 2,3-dihydroxypropyl, 4-hydroxybutyl, 5-hydroxypentyl, 2-hydroxypentyl, 2,3,4,5,6-pentahydroxyhexyl, 8-hydroxyoctyl, 2-hydroxyoctyl, 2-hydroxynonyl, 2-hydroxydecyl or 2-hydroxyoctadecyl. $C_1$-$C_8$hydroxyalkyl in which the hydroxyl group is in the terminal position or in the 2-position is preferred as is $C_9$-$C_{20}$alkyl which is substituted by —OH in the 2-position. $C_1$-$C_6$alkyl which is substituted by —OH is particularly preferred.

Examples of R as $C_3$-$C_{20}$alkenyl are allyl, 2-methallyl, 3methylbut-2-enyl, 3-methylbut-3-enyl, hexenyl, decenyl, undecenyl, heptadecenyl or oleyl. Preferred meanings are allyl, methallyl and oleyl.

Examples of R as $C_3$-$C_8$cycloalkyl which is unsubstituted or substituted by $C_1$-$C_4$alkyl are cyclopropyl, cyclobutyl, cyclopentyl, cyclohexyl, methylcyclohexyl, 4-butylcyclohexyl, cycloheptyl, cyclooctyl or cyclododecyl. $C_5$-$C_7$cycloalkyl, in particular cyclohexyl, is preferred.

R as $C_7$-$C_{11}$phenylalkyl is, for example, benzyl or phenylethyl.

Examples of R as $C_7$-$C_{11}$phenylalkyl which is substituted by 1 to 3 radicals according to the definition are o-, m- or p-chlorobenzyl, 2,3-dichlorobenzyl, 2,4-dichlorobenzyl, 2,5-dichlorobenzyl, 2,6-dichlorobenzyl, 3,4-dichlorobenzyl, 2,4,5-trichlorobenzyl, 2,4,6-trichlorobenzyl, o-, m- or p-hydroxybenzyl, o-, m- or p-methylbenzyl, 2,3-dimethylbenzyl, 2,4-dimethylbenzyl, 2,5-dimethylbenzyl, 2,6-dimethylbenzyl, 3,4-dimethylbenzyl, 3,5-dimethylbenzyl, 2-methyl-4-tert-butylbenzyl, 2-ethylbenzyl, 2,6-diethylbenzyl, 2,6-diethyl-4-methylbenzyl, 2,6-diisopropylbenzyl, 4-tert-butylbenzyl, 2-chloro-6-methylbenzyl, 3-chloro-2-methylbenzyl, 3-chloro-4-methylbenzyl, 4-chloro-2-methylbenzyl, 5-chloro-2-methylbenzyl, 2,6-dichloro-3-methylbenzyl, 2-hydroxy-4-methylbenzyl, 3-hydroxy-4-methylbenzyl, o-, m- or p-methoxybenzyl, o-, m-or p-ethoxybenzyl, 2,4-dimethoxybenzyl, 2,5-dimethoxybenzyl, 2,5-diethoxybenzyl, 2-methoxy-5-methylbenzyl, 4-methoxy-2-methylbenzyl, 3-chloro-4-methoxybenzyl, 3-chloro-6-methoxybenzyl, 3-chloro-4,6-dimethoxybenzyl or 4-chloro-2,5-dimethoxybenzyl.

Examples of $R_1$, $R_2$ and $R_3$ as $C_1$-$C_{20}$alkyl are, in addition to the meanings given above for R=alkyl, methyl, ethyl, propyl, isopropyl, butyl, tert-butyl, pentyl, hexyl and heptyl.

Examples of X, $R_1$, $R_2$ and $R_3$ as $C_1-C_{20}$alkyloxy are methoxy, ethoxy, butoxy, pentyloxy, hexyloxy, heptyloxy, octyloxy, nonyloxy, decyloxy, dodecyloxy, tridecyloxy, hexadecyloxy or octadecyloxy. One of the preferred meanings for $R_1$, $R_2$ and $R_3$ is $C_1-C_4$alkyloxy, in particular methoxy and ethoxy.

Examples of X, $R_1$, $R_2$ and $R_3$ as $C_1-C_{20}$alkylthio are methylthio, ethylthio, propylthio, butylthio, pentylthio, hexylthio, heptylthio, octylthio, nonylthio, decylthio, dodecylthio, tridecylthio, hexadecylthio or octadecylthio. $C_8-C_{18}$alkylthio is preferred.

Examples of $R_1$, $R_2$ and $R_3$ as $C_2-C_{12}$alkyloxycarbonyl are methoxycarbonyl, ethoxycarbonyl, propoxycarbonyl, butoxycarbonyl, pentyloxycarbonyl, hexyloxycarbonyl, octyloxycarbonyl and decyloxycarbonyl.

Examples of $R_1$, $R_2$ and $R_3$ as $C_2-C_{12}$alkanoyl are acetyl, propanoyl, butanoyl, pentanoyl, hexanoyl, heptanoyl, octanoyl or decanoyl.

Examples of group IIb are o-, m- or p-chlorophenyl, 2,3-dichlorophenyl, 2,4-dichlorophenyl, 2,5-dichlorophenyl, 3,4-dichlorophenyl, 2,4,5-trichlorophenyl, 2,4,6-trichlorophenyl, o-, m- or p-hydroxyphenyl, o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-4-tert-butylphenyl, 2-ethylphenyl, 2,3-diethylphenyl, 2,4-diethylphenyl, 2,5-diethylphenyl, 2,6-diethylphenyl, 3,5-diethylphenyl, 2,6-diethyl-4-methylphenyl, 2,6-diisopropylphenyl, 4-tert-butylphenyl, 3,5-di-tert-butylphenyl, 2-chloro-6-methylphenyl, 3-chloro-2-methylphenyl, 3-chloro-4-methylphenyl, 4-chloro-2-methylphenyl, 5-chloro-2-methylphenyl, 2,6-dichloro-3-methylphenyl, o-, m- or p-methoxyphenyl, o-, m- or p-ethoxyphenyl, o-, m-or p-propoxyphenyl, o-, m- or p-butoxyphenyl, o-, m- or p-hexyloxyphenyl, o-, m-or p-octyloxyphenyl, 2,4-dimethoxyphenyl, 2,5-dimethoxyphenyl, 2,5-diethoxyphenyl, 2-methoxy-5-methylphenyl, 4-methoxy-2-methylphenyl, 3-chloro-4-methoxyphenyl, 3-chloro-6-methoxyphenyl, 3-chloro-4,6-dimethoxyphenyl, 4-chloro-2,5-dimethoxyphenyl, o-, m- or p-methylthiophenyl, o-, m-or p-ethylthiophenyl, o-, m- or p-propylthiophenyl, o-, m- or p-butylthiophenyl, o-, m- or p-pentylthiophenyl, o-, m- or p-hexylthiophenyl, o-, m- or p-heptylthiophenyl, o-, m- or p-octylthiophenyl, o-, m-or p-nonylthiophenyl, o-, m- or p-decylthiophenyl, o-, m- or p-phenylphenyl and 2-hydroxy-4-methylphenyl, 3-hydroxy-4-methylphenyl and a group of the formula

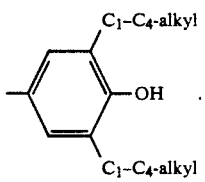

Preferred meanings for group IIb can be seen from Examples 1 to 8 given below.

In the group of the formula IIb, $R_1$ and/or $R_2$ are particularly prefererably hydrogen.

Compositions which are of interest are those in which R is $C_{10}-C_{18}$-alkyl, OH-substituted $C_1-C_{10}$alkyl, $C_3-C_{10}$alkenyl, $C_5-C_7$cycloalkyl, $C_1-C_4$alkyl-substituted $C_5-C_7$cycloalkyl, benzyl, benzyl which is substituted on the phenyl by 1 to 3 radicals, these radicals, independently of one another, being hydroxyl, chlorine, $C_1-C_4$alkyl, methoxy or ethoxy, or R is furthermore a group of the formula IIa or IIb, in which X is $C_1-C_{10}$alkyloxy, $C_8-C_{18}$alkylthio, phenyloxy, phenylthio, benzyloxy or benzylthio and $R_1$, $R_2$ and $R_3$, independently of one another, are hydrogen, $C_1-C_{10}$alkyl, $C_1-C_{10}$alkyloxy, $C_8-C_{18}$alkylthio, $C_2-C_{12}$alkyloxycarbonyl, $C_2-C_6$alkanoyl, phenyloxy, phenylthio, hydroxyl, mercapto or chlorine.

Compositions in which R is $C_{10}-C_{18}$alkyl, OH-substituted $C_1-C_6$alkyl, allyl, cyclohexyl or benzyl are also of interest.

R is preferably the group IIb.

Preference is also given to compositions in which R is a group of the formula IIb and the radicals $R_1$, $R_2$ and $R_3$, independently of one another, are hydrogen, $C_1-C_4$alkyl, $C_1-C_4$alkyloxy, $C_8-C_{16}$alkylthio, $C_2-C_{12}$alkyloxycarbonyl, hydroxyl, mercapto or chlorine.

Particular preference is given to compositions in which R is a group of the formula IIb, $R_1$ is hydrogen, $R_2$ and $R_3$, independently of one another, are $C_1-C_4$alkyl, $C_1-C_4$alkyloxy, $C_8-C_{16}$alkylthio, $C_2-C_{12}$alkyloxycarbonyl, hydroxyl or chlorine and $R_2$ is additionally hydrogen.

Compositions which are of particular interest are those in which R is a group of the formula IIb, $R_1$ and $R_2$ are hydrogen and $R_3$ is $C_1-C_4$alkyl, $C_1-C_4$alkyloxy, $C_8-C_{16}$alkylthio, $C_2-C_{12}$alkyloxycarbonyl, hydroxyl or chlorine, in particular $C_1-C_4$alkyloxy or hydroxyl.

According to a further preference, component b) can be present as hydrochloride.

Component c) is preferably an Me(II) carboxylate, in which Me(II) is Ba, Ca, Mg, Cd or Zn. The carboxylates are preferably salts of carboxylic acids having 7 to 20 C atoms, for example benzoates, alkanoates or alkenoates, preferably stearates, oleates, laurates, palmitates, hydroxystearates or 2-ethylhexanoates. Stearates, oleates or p-tert-butylbenzoates are particularly preferred.

Mixtures of Ba/Zn or Ca/Zn carboxylates are also particularly preferred as component c).

An Me(II) phenolate as component c) is in particular a $C_7-C_{20}$(o-, m- or p-)alkylphenolate, for example, o-, m- or p-nonylphenolate.

According to a further preference, the compositions according to the invention contain an epoxy compound and/or a phosphite as additional component d).

The epoxy compound is preferably an epoxidised oil or an epoxidised fatty acid ester, for example epoxidised soya bean oil, epoxidised butyl oleate and epoxidised octyl oleate.

The phosphites are preferably those of the formula

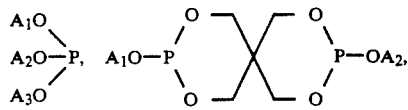

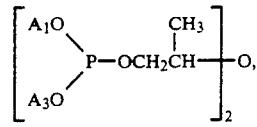

-continued

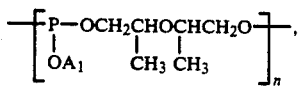

in which $A_1$, $A_2$ and $A_3$, independently of one another, are $C_4$-$C_{18}$alkyl, $C_6$-$C_{18}$alkenyl, $C_5$-$C_7$cycloalkyl, phenyl or phenyl which is substituted by one to three $C_1$-$C_{12}$alkyl groups.

Examples are trioctyl, tridecyl, tridodecyl, tritetradecyl, tristearyl, trioleyl, triphenyl, tricresyl, tris-p-nonylphenyl and tricyclohexyl phosphite. Preference is given to the aryl dialkyl and the alkyl diaryl phosphites, for example phenyl didecyl, (2,4-di-tert-butylphenyl) didodecyl, (2,6-di-tert-butylphenyl) didodecyl phosphite and the dialkyl and diaryl pentaerythritol diphosphites, for example distearyl pentaerythritol diphosphite. Preference is also given to the tetraphenyl and tetraalkyl [1,2-dipropylene glycol] diphosphites and the poly[1,2-dipropylene glycol phenyl phosphites] and the poly[1,2-dipropylene glycol alkyl phosphites].

Particularly preferred organic phosphites are distearyl pentaerythritol diphosphite, tris(nonylphenyl)-phosphite, phenyldidecylphosphite, tetraphenyl [1,2-dipropylene glycol] diphosphite and poly[1,2-dipropylene glycol phenyl phosphite].

The Me(II) carboxylates or phenolates are preferably used in amounts of 0.05 to 5% by weight.

The phosphites are used, for example, in concentrations of 0.3 to 5, preferably 0.5 to 1, % by weight, and the epoxy compounds, for example epoxidised soya bean oil, advantageously in concentrations of 1 to 8, preferably 1 to 3, % by weight.

The compounds of the formula I are preferably incorporated in the chlorine-containing polymer in amounts of 0.05 to 1 or 0.01 to 0.9, in particular 0.1 to 0.7, % by weight.

The % by weight given refers in each case to the material to be stabilised.

The chlorine-containing polymers are preferably vinyl chloride homopolymers or copolymers. Examples of suitable comonomers for the copolymers are: vinyl acetate, vinylidene chloride, trans-dichloroethene, ethylene, propylene, butylene, maleic acid, acrylic acid, fumaric acid, itaconic acid. Further suitable chlorine-containing polymers are postchlorinated PVC and chlorinated polyolefins, furthermore graft polymers of PVC with EVA, ABS and MBS. Preferred substrates are also mixtures of the abovementioned homo-and copolymers, in particular vinyl chloride homopolymers, with other thermoplastic and/or elastomeric polymers, in particular with ABS, MBS, NBR, SAN, EVA.

Further preference is given to suspension and bulk polymers and to emulsion polymers.

Polyvinyl chloride is particularly preferred as chlorine-containing polymer.

The invention further relates to the use of a stabiliser system containing components b) and c) for stabilising a chlorine-containing polymer against thermodegradation.

Depending on the intended use of the polymers, further additives can be incorporated before or during the incorporation of the stabilisers, for example phenolic antioxidants, lubricants (preferably montan waxes or glycerol esters, fatty acid esters, paraffins, amide waxes, stearic acid, mono- and dihydroxystearic acid, higher fatty alcohols), plasticisers, fillers, carbon black, asbestos, kaolin, talc, glass fibres, modifiers, (impact-resistant additives), processing aids (for example polymethacrylic esters), fluorescent whitening agents, pigments, light stabilisers, sterically hindered amines, UV absorbers, flame retardants or antistatics.

Further possible additives are furthermore $\beta$-aminocrotonates, for example the compounds described in DE-A 804,442, DE-A 807,207 and JP-A 75/17,454, pyrroles, for example the compounds mentioned in EP-A 22,087, aminouracils, for example the compounds disclosed in EP-A 65,934, aminothiouracils, for example the compounds known from EP-A 41,479, polyols, for example the compounds described in DE-A 3,019,910, $\beta$-diketones, for example the compounds mentioned in DE-A 2,600,516, hydrotalcites, in particular the compounds described in DE-A 3,843,581, or also mixtures of $\beta$-diketones and hydrotalcites, as described in EP-A 63,180, furthermore Mg/Al carbonates, for example the Mg/Al carbonates disclosed in JP-A-Sho 62/267,347 (=Chemical Abstracts 108:168 635 h), and Alcamizers, for example 4 MgO $Al_2O_3$.$CO_2$.9 $H_2O$, 4 MgO $Al_2O_3$.-$CO_2$.6 $H_2O$, ZnO 3MgO $Al_2O_3$.$CO_2$.8-9 $H_2O$, ZnO 3 MgO $Al_2O_3$.$CO_2$.5-6 $H_2O$ and $Mg_4Al_2(OH)_{12}$-$(CO_3)_{1-x/2}(ClO_4)_x$m$H_2O$.

Possible additives are also chemical blowing agents for expanded rigid or plasticised polyvinyl chloride, for example $NaHCO_3$ and the blowing agents mentioned in "Gächter/Müller; Taschenbuch der Kunststoff-Additive (Handbook of plastic additives), Carl Hanser Verlag Munich-Vienna, 2nd edition, 1983" on page 651.

The stabiliser components are most favourably incorporated in the chlorine-containing polymer, as is usual, on mixed rolls, for example in a 2-roll mill at temperatures between 150° and 200° C. In general, sufficient homogenisation can be obtained within 5 to 15 minutes. The components can be added individually or together as a premixture. A liquid premixture has proven to be advantageous, i.e. the homogenisation is carried out in the presence of inert solvents and/or plasticisers.

The compositions according to the invention can be processed to give moulded articles by the moulding processes customary for this, for example by extrusion, injection-moulding or calandering. The use of plastisols is also possible.

The compositions according to the invention are preferably used for the manufacture of electro cables, hollow articles, for example pipes, and in particular sheets in the automobile industry. This use is also provided by the invention. A particularly preferred area of application is the manufacture of sheets for the interior of automobiles, in particular for those as described in DE-A 3,227,107 and DE-A 3,401,482.

The compositions according to the invention are particularly advantageously used for the manufacture of deep-drawing sheets and flexible sheets based on PVC, in particular for the use in the automobile industry.

The compounds of the formula I can be prepared in analogy to known processes. Preparation processes are described, for example, in the following publications: D. F. Walker et al.; J. Am. Pharm. Assoc. 39, 393 (1950), D. W. Kaiser et al.; J. Am. Chem. Soc. 73, 2984 (1951), A. B. Borkovec et al.; J. Med. Chem. 10, 457 (1967).

When R has one of the abovementioned meanings other than the group IIb, it is advantageous to prepare the melamine derivatives by the following scheme:

Scheme A

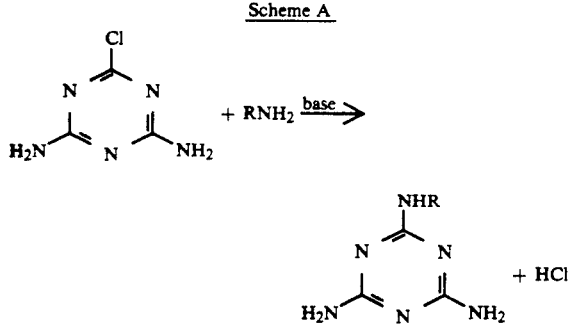

In general, water is a suitable reaction medium. In some cases, in particular if R is a long-chain alkyl radical, it is advantageous to add a solubilizer, for example dimethylacetamide. The base is, for example, alkali metal hydroxide, preferably sodium hydroxide.

The melamine obtained can be converted to the corresponding hydrochloride by heating it with concentrated hydrochloric acid (slight excess). Inversely, it is possible to obtain again the melamine from the hydrochloride by treating with, for example, alkali metal hydroxide or alkali metal bicarbonate solution, which would constitute a further purification step.

In some cases, it is also possible to prepare compounds of the formula I in which R is a group of the formula IIb by the above scheme A; however, in these cases, the basicity of the amine must be higher.

Compounds of the formula I in which R is a group of the formula IIb are preferably prepared by Scheme B given below.

Scheme B

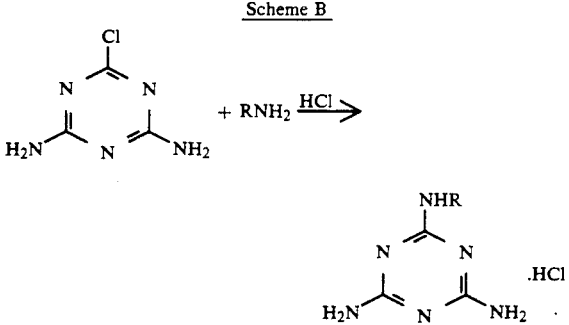

In this case, too, water is a suitable reaction medium, it being possible, if required, to add again a solubiliser. The hydrochloride is advantageously converted into the corresponding melamine derivative as described above.

In general, the compounds of the formula I and their hydrochlorides have a defined hydrated water content.

The starting materials are commercially available or can be prepared in analogy to processes known to one skilled in the art. The preparation of diaminochlorotriazine is described, for example, by J. T. Thurston et al. in "J. Am. Chem. Soc. 73, 2981 (1951)".

The compounds of the formula I can also be used against photolytic degradation of chlorine-containing polymers.

The invention also relates to the novel compounds of the formula Ia and hydrochlorides thereof,

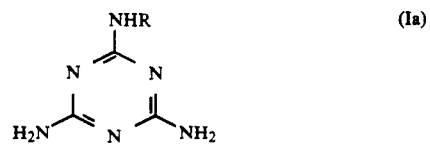

in which R is $C_7$–$C_{11}$phenylalkyl which is substituted on the phenyl by 1 to 3 radicals, the radicals, independently of one another, being hydroxyl, chlorine, $C_1$–$C_4$alkyl, methoxy or ethoxy, or R is furthermore a group of the formula IIa, II-b-1, II-b-2 or II-b-3.

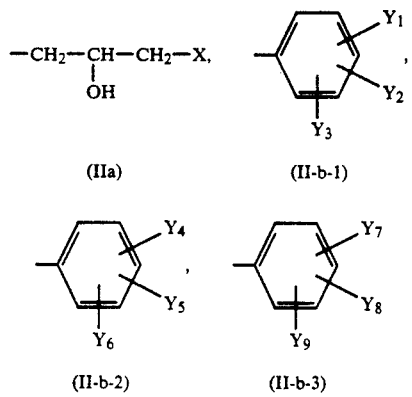

in which X is $C_1$–$C_{20}$alkyloxy, $C_1$–$C_{20}$alkylthio, phenyloxy, phenylthio, benzyloxy or benzylthio, $Y_1$, $Y_2$ and $Y_3$, independently of one another, are $C_1$–$C_{20}$alkylthio, $C_2$–$C_{12}$alkyloxycarbonyl or mercapto, and $Y_1$ and $Y_2$ are additionally hydrogen, $Y_4$ is methoxy, ethoxy or hydroxyl, $Y_5$ and $Y_6$, independently of one another are $C_1$–$C_{20}$alkyl, $C_1$–$C_{20}$alkyloxy, $C_1$–$C_{20}$alkylthio, $C_2$–$C_{12}$alkyloxycarbonyl, $C_2$–$C_{12}$alkanoyl, phenyl, phenyloxy, phenylthio, hydroxyl, mercapto or chlorine, and $Y_5$ is additionally hydrogen, $Y_7$, $Y_8$ and $Y_9$, independently of one another, are $C_2$–$C_{20}$alkyl or $C_2$–$C_{12}$alkyloxycarbonyl and $Y_9$ is additionally hydrogen.

For the compounds of the formula Ia, the same preferences apply as for the compounds of the formula I, and the radicals $Y_1$ to $Y_9$ correspond to the radicals $R_1$ to $R_3$.

The examples which follow illustrate the invention in more detail. Parts and percentages are by weight, unless stated otherwise.

EXAMPLE 1

Preparation of N-(n-dodecyl)melamine (Compound 1-A-1)

A mixture of 14.6 g (0.1 mol) of diaminochlorotriazine, 19.5 g (0.105 mol) of n-dodecylamine and 4.0 g (0.1 mol) of sodium hydroxide in 200 ml of water is refluxed for 5 hours. The solid formed is filtered off wich suction, washed until free of chloride and then treated with a mixture of methylene chloride/ether (1:1). The precipitate is filtered off and boiled in dimethylformamide. After filtration, the concentrated filtrate is poured into water with stirring. The precipitate formed is dried to constant weight. The yield is 65% of theory. The product contains 0.1 mol of hydrated water per mole of melamine and melts at 119° C.

EXAMPLE 2

The compounds in Table 1 are prepared in analogy to the process described in Example 1.

TABLE 1

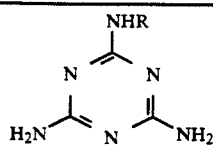

| Compound No. | R | Melting point | Yield [% of theory] | |
|---|---|---|---|---|
| 1-A-2 | —(CH$_2$)$_3$—OH | 160° C. | 87 | |
| 1-A-3 | —(CH$_2$)$_5$—OH | — | — | |
| 1-A-4 | —(CH$_2$—CH=CH$_2$) | 172° C. | 57.2 | (The product is present in the form of a hydrate (0.25 mol of H$_2$O per mol of melamine). |
| 1-A-5 | —⟨H⟩ (cyclohexyl) | 146° C. | 66 | (After recrystallisation from acetic acid. The product is present in the form of a hydrate (0.6 mol of H$_2$O per mol of melamine).) |
| 1-A-6 | —CH$_2$—phenyl | | | |

EXAMPLE 3

Preparation of N-benzylmelamine hydrochloride (Compound 1-A-7)

10.8 g (0.05 mol) of compound 1-A-6 are refluxed together with 6.84 g (0.06 mol) of 32% hydrochloric acid for 1 hour with stirring. The clear solution is cooled to 0° C., and the crystals formed are filtered off, washed and dried. The yield is 73.8% of theory. The product has a melting point of 275° C.

EXAMPLE 3a

Preparation of N-[3-(2'-ethylhexyl)oxy-2-hydroxypropyl]melamine (Compound 1-A-8)

A mixture of 29.1 g (0.2 mol) of diaminochlorotriazine, 40.7 g (0.2 mol) of 3-(2'-ethylhexyl)oxy-2-hydroxypropylamine and 300 ml of water is refluxed. 0.2 mol of NaOH in 80 ml of water are added dropwise over a period of 1 hour. The reaction mixture is then refluxed for 2 hours. 25 ml of concentrated hydrochloric acid are added to the resulting oil, giving a clear solution. Upon cooling, the hydrochloride of N-[3-(2'-ethylhexyl)oxy-2-hydroxypropyl]melamine precipitates and is then neutralised with NaHCO$_3$ at 40° C. The wax-like product obtained is washed until free of chloride with ice water and dried in vacuo. The yield is 86.6% of theory. The product has a melting point of 109°–115° C.

EXAMPLE 3b

Preparation of N-n-hexylmelamine (Compound 1-A-9)

The preparation is carried out in analogy to Example 3a. The yield is 70.8% of theory. The product has a melting point of 116°–119° C.

EXAMPLE 4

Preparation of N-phenylmelamine (=Compound 2-A-1)

A mixture of 14.6 g (0.1 mol) of diaminochlorotriazine, 9.8 g (0.105 mol) of aniline and 4.0 g (0.1 mol) of sodium hydroxide in 30 ml of water is refluxed for 2 hours with the addition of 200 ml of water. The cloudy solution is cooled, the precipitated solid is filtered off, washed until free of chloride and dried to constant weight. The product obtained is purified by dissolving it in glacial acetic acid and then treating it with bicarbonate. The yield is 62% of theory. The product has a melting point of 202° C.

EXAMPLE 5

The compounds listed in Tables 2a to 2c are prepared in analogy to the process described in Example 4. The data given in Tables 2a to 2c refer to the general formula given below.

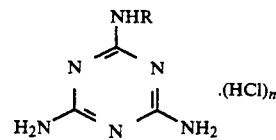

TABLE 2a

| Comp. No. | n | R | Melting point | Yield [% of theory] |
|---|---|---|---|---|
| 2a-A-1 | 0 | 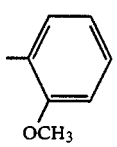 (phenyl-OCH$_3$) | 163° C. | 98 (The product is present as a hemihydrate). |

TABLE 2a-continued

| Comp. No. | n | R | Melting point | Yield [% of theory] |
|---|---|---|---|---|
| 2a-A-2 | 0 | (phenyl with OCH₃ at ortho) | 184° C. | 96 |
| 2a-A-3 | 0 | (phenyl with OCH₃ at para) | 205° C. | 95 |
| 2a-A-4 | 0 | (phenyl with OH at ortho) | 260° C. | 76 (After recrystallisation from ethanol.) |
| 2a-A-5 | 1 | (phenyl with OH at meta) | 271° C. | 36 (The product is present as a hydrate (1.3 mol of H₂O per mol of melamine).) |
| 2a-A-6 | 0 | (phenyl with OH at para) | 288° C. | 39 (After recrystallisation from methanol.) |

TABLE 2b

| Comp. No. | n | R | Melting point | Yield [% of theory] |
|---|---|---|---|---|
| 2b-A-1 | 0 | (phenyl with OCH₃ and OCH₃) | 215° C. | 97 |

TABLE 2c

| Comp. No. | n | R | Melting point | Yield [% of theory] |
|---|---|---|---|---|
| 2c-A-1 | 0 | (phenyl with CH₃ and OH) | 200° C. | 70 (After recrystallisation from ethanol/water. The product is present as a hemihydrate.) |
| 2c-A-2 | 0 | (phenyl with Cl and OH) | 240° C. | 58 (After recrystallisation from ethanol/water. The product is present as a hydrate (0.75 mol of H₂O per mol of melamine).) |

EXAMPLE 6

Preparation of N-phenylmelamine (Compound 1-B-1 (=2 -A-1)

A mixture of 19.7 g (0.135 mol) of diaminochlorotriazine, 15.5 g (0.140 mol) of aniline, 1.3 ml of conc. hydrochloric acid (catalyst) is refluxed in 200 ml of water for 1 hour with stirring. The solution is filtered, and the filtrate is neutralised conc.sodium bicarbonate solution (pH=7.2). The precipitate formed is filtered off with suction, washed until free of chloride and dried to constant weight. The product obtained has a melting point of 206° C. The yield is 86.4% of theory.

EXAMPLE 7

Preparation of N-phenylmelamine hemihydrochloride (Compound 1-B-2)

A mixture of 36.4 g (0.25 mol) of diaminochlorotriazine, 24.4 g (0.26 mol) of aniline and 7 ml of concentrated hydrochloric acid is refluxed in 500 ml of water for 1 hour. The solution is filtered, and the filtrate is cooled. The colourless crystals obtained are washed and dried to constant weight. The yield is 68.3% of theory. The product has a melting point of 259° C. and is present as a dihydrate.

EXAMPLE 8

The compounds in Table 3a to 3d are prepared in analogy to the process described in Example 6 or 7. The data given in Table 3a to 3d refer to the general formula given below.

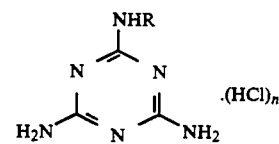

TABLE 3a

| Comp. No. | n | R | Melting point | Yield [% of theory] | |
|---|---|---|---|---|---|
| 3a-B-1 | 0 | 2-methylphenyl (o-tolyl) | 210° C. | ~65 | (The product is present in the form of a hydrate (0.1 mol of $H_2O$ per mol of melamine).) |
| 3a-B-2 | 0 | 3-methylphenyl (m-tolyl) | 220° C. | 88.2 | (The product is present as a hydrate (0.2 mol of $H_2O$ per mol of melamine).) |
| 3a-B-3 | 0 | 4-methylphenyl (p-tolyl) | 290° C. | 83.8 | (The product is present as a hydrate (0.15 mol of $H_2O$ per mol of melamine).) |
| 3a-B-4 | 0 | 4-(n-$C_4H_9$)-phenyl | 161° C. | 43 | (After recrystallisation from methanol.) |
| 3a-B-5 | 0 | 4-(t-$C_4H_9$)-phenyl | 250° C. | 76 | |
| 3a-B-6 | 0 | 4-(S—$C_{16}H_{33}$-n)-phenyl | 80° C. | 81 | (Addition of dimethyl-acetamide. The product is present as a sesquihydrate.) |
| 3a-B-7 | 0 | 2-($COOCH_3$)-phenyl | 320° C. (decomposition) | 75 | (In the reaction, the free acid is also formed, which can be separated off by customary methods. The product is present as a hydrate (0.2 mol of $H_2O$ per mol of melamine).) |
| 3a-B-8 | 0 | 3-($COOC_2H_5$)-phenyl | 165° C. | 58 | (After recrystallisation from acetic acid. The product is present as a hydrate (0.2 mol of $H_2O$ per mol of melamine).) |
| 3a-B-9 | 0 | 2-($COOC_4H_9$-n)-phenyl | 190° C. | 28 | (Addition of dimethylacetamide. The product is present as a hydrate (0.1 mol of $H_2O$ per of melamine).) |
| 3a-B-10 | 0 | 4-($COOC_4H_9$-n)-phenyl | 280° C. | 77 | |

TABLE 3a-continued

| Comp. No. | n | R | Melting point | Yield [% of theory] | |
|---|---|---|---|---|---|
| 3a-B-11 | 0 | (2-COOC$_8$H$_{17}$-i* phenyl) | 152° C. | 64 | (Prepared by transesterification of 3a-B-7 in the presence of Ti(OC$_4$H$_9$)$_4$.) |
| 3a-B-12 | 0 | (4-COOC$_8$H$_{17}$-i phenyl) | 65° C. | 36.5 | (Prepared by transesterification of 3a-B-8 in the presence of Ti(OC$_4$H$_9$)$_4$. Purified by recrystallisation from methylene chloride/petroleum ether). |
| 3a-B-13 | 0 | (2-COOC$_{10}$H$_{21}$-n phenyl) | 160° C. | 43.8 | (Addition of dimethylacetamide.) |
| 3a-B-14 | 1 | (2-OH phenyl) | 294° C. | 73.1 | (After recrystallisation from water in the presence of activated carbon. The product is present as a hydrate (0.8 mol of H$_2$O per mol of melamine).) |
| 3a-B-15 | 0 | (3-OH phenyl) | 242° C. | 89.9 | (Prepared from the hydrochloride with bicarbonate solution). |
| 3a-B-16 | 1 | (4-OH phenyl) | 290° C. | 73.8 | (After recrystallisation from water in the presence of activated carbon. The product is present as a monohydrate.) |
| 3a-B-17 | 0 | (2-SH phenyl) | 278° C. | 49.3 | (Addition of dimethylacetamide. The product is present as a hemihydrate.) |
| 3a-B-18 | 0 | (2-Cl phenyl) | 203° C. | 89.8 | |
| 3a-B-19 | 0 | (3-Cl phenyl) | 165° C. | 85.0 | |
| 3a-B-20 | 0 | (4-Cl phenyl) | 238° C. | 87.9 | |

*—C$_8$H$_{17}$-i = 2-ethylhexyl

TABLE 3b

| Comp. No. | n | R | Melting point | Yield [% of theory] | |
|---|---|---|---|---|---|
| 3b-B-1 | 0 | 2,3-dimethylphenyl | 260° C. | 78.2 | (The product is present as a hydrate (1.2 mol of $H_2O$ per mol of melamine).) |
| 3b-B-2 | 0 | 2,3-dimethylphenyl (alt) | 251° C. | 76.8 | (The product is present as a hydrate (0.15 mol of $H_2O$ per mol of melamine).) |
| 3b-B-3 | 0 | 2,4-dimethylphenyl | 233° C. | 87.0 | (The product is present as a hydrate (0.15 mol of $H_2O$ per mol of melamine).) |
| 3b-B-4 | 0 | 2,4-dimethylphenyl (alt) | 260° C. | 88.8 | (The product is present as a hydrate (0.1 mol of $H_2O$ per mol of melamine).) |
| 3b-B-5 | 0 | 2,5-dimethylphenyl | 277° C. | ~80 | (The product is present as a hydrate (0.15 mole of $H_2O$ per mol of melamine).) |
| 3b-B-6 | 0 | 2,5-dimethylphenyl (alt) | 230° C. | 88.5 | (The product is present as a hydrate (0.1 mol of $H_2O$ per mol of melamine).) |
| 3b-B-7 | 1 | dimethoxyphenyl | 265° C. | 61.5 | (After recrystallisation from water in the presence of activated carbon. The product is present as a monohydrate.) |
| 3b-B-8 | 1 | dimethoxyphenyl (alt) | 256° C. | 76.0 | (After recrystallisation from water in the presence of activated carbon. The product is present as a hydrate (0.2 mol of $H_2O$ per mol melamine).) |
| 3b-B-9 | 0 | dimethoxyphenyl | 186° C. | 99.0 | (Prepared by treating 3b-B-8 with bicarbonate solution). |

TABLE 3b-continued

| Comp. No. | n | R | Melting point | Yield [% of theory] | |
|---|---|---|---|---|---|
| 3b-B-10 | 1 | phenyl with OCH₃ (2,5-di-OCH₃) | 277° C. | 71.4 | (After recrystallisation from water in the presence of activated carbon.) |
| 3b-B-11 | 0 | phenyl with 2,5-di-OCH₃ | 103° C. | 87.0 | (Prepared by treating 3b-B-10 with bicarbonate solution. This product is present as a monohydrate). |
| 3b-B-12 | 1 | phenyl with 3,4-di-OCH₃ | — | 79.5 | (After recrystallisation from water in the presence of activated carbon. The product is present as a hydrate (0.2 mol of H₂O per mol of melamine).) |
| 3b-B-13 | 0 | phenyl with 3,4-di-OCH₃ | 225° C. | 99.4 | (Prepared by treating 3b-B-12 with bicarbonate solution. The product is present as a hydrate (0.2 mol of H₂O per mol of melamine).) |
| 3b-B-14 | 0 | phenyl with 3,5-di-COOCH₃ | 267° C. | 50 | (The product is present as a hemihydrate.) |
| 3b-B-15 | 0 | phenyl with 3,5-di-COOC₈H₁₇-i | 89° C. | 51 | (Prepared by transesterification of 3b-B-14 in the presence of Ti(OC₄H₉)₄. Purification by recrystallisation from methylene chloride/ether.) |
| 3b-B-16 | 0 | phenyl with 3,4-di-Cl | 245° C. | 85.0 | (Addition of dimethylacetamide. The product is present as a hydrate (0.25 mol of H₂O per mol of melamine).) |
| 3b-B-17 | 0 | phenyl with 2,5-di-Cl | 234° C. | 80.1 | (Addition of dimethylacetamide). |
| 3b-B-18 | 0 | phenyl with 3,5-di-Cl | 228° C. | 86.2 | (Addition of dimethylacetamide). |

TABLE 3b-continued

| Comp. No. | n | R | Melting point | Yield [% of theory] | |
|---|---|---|---|---|---|
| 3b-B-19 | 0 | 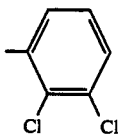 2,3-dichlorophenyl | 229° C. | 86.5 | (Addition of dimethylacetamide). |
| 3b-B-20 | 0 | 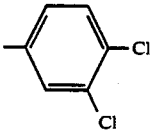 3,4-dichlorophenyl | 201° C. | 81.3 | (Addition of dimethylacetamide). |

TABLE 3c

| Comp. No. | n | R | Melting point | Yield [% of theory] | |
|---|---|---|---|---|---|
| 3c-B-1 | 0 | 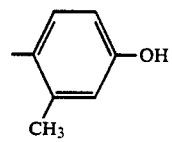 | 257° C. | 61 | (The product is present as a hydrate (0.7 mol of H₂O per mol of melamine).) |
| 3c-B-2 | 0 | 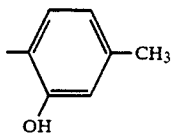 | 255° C. | ~80 | (The product is present as a hydrate (0.15 mol of H₂O per mol of melamine).) |
| 3c-B-3 | 0 | 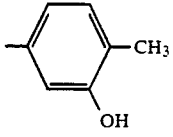 | 232° C. | 69.0 | (The product is present as a hydrate (0.25 mol of H₂O per mol of melamine).) |
| 3c-B-4 | 0 | 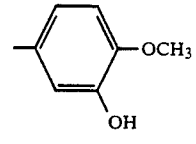 | 240° C. | ~70 | (The product is present as a hydrate (0.25 mol of H₂O per mol of melamine).) |
| 3c-B-5 | 0 | 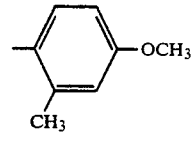 | 262° C. | 75.2 | (The product is present as a hydrate (0.1 mol of H₂O per mol of melamine).) |
| 3c-B-6 | 0 | 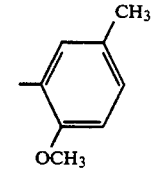 | 268° C. | 89.3 | (The product is present as a hydrate (0.15 mol of H₂O per mol of melamine).) |

TABLE 3d

| Comp. No. | n | R | Melting point | Yield [% of theory] | |
|---|---|---|---|---|---|
| 3d-B-1 | 0 | 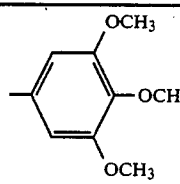 | 230° C. (After purification via the hydrochloride 210° C.) | 84.3 | (The product is present as a hemihydrate. |

TABLE 3d-continued

| Comp. No. | n | R | Melting point | Yield [% of theory] |
|---|---|---|---|---|
| 3d-B-2 | 1 | 2,3,4-trimethoxyphenyl (OCH$_3$, OCH$_3$, OCH$_3$) | 258° C. | 77.4 (Prepared by treating 3d-B-1 with HCl. Recrystallisation from water in the presence of activated carbon. The product is present as a hydrate (0.75 mol of H$_2$O per mol of melamine).) |
| 3d-B-3 | 0 | 2,4,5-trichlorophenyl (Cl, Cl, Cl) | 200° C. | 30.1 (Addition of dimethylacetamide. Purification by reprecipitation using dimethyl sulfoxide/H$_2$O). |
| 3d-B-4 | 0 | 2,3,4-trichlorophenyl (Cl, Cl, Cl) | 150° C. | 22.1 (Addition of dimethylacetamide. Purification by reprecipitation using dimethyl sulfoxide/H$_2$O). |
| 3d-B-5 | 0 | 2,6-dichloro-4-hydroxyphenyl (Cl, OH, Cl) | >300° C. | 91.7 (The product is present as a hydrate (0.4 mol of H$_2$O per mol of melamine).) |

EXAMPLE 9

A dry mixture comprising 100 parts of S-PVC (®Vinnol H 70 DF), 17 parts of dioctyl phthalate, 3 parts of epoxidised soya bean oil, 0.33 part of zinc oleate, 0.53 part of barium p-(t-butyl)benzoate, 0.7 part of diisodecylphenyl phosphite, 0.44 part of ®SHELL SOL A (aromatic hydrocarbon mixture) and 0.2 part of the melamine derivative listed in Tables 4a to 4h is rolled on mixing rolls at 190° C. for 5 minutes. Test specimens of the 0.3 mm thick rolled sheet formed are subjected to thermal stress at 180° C. in a test oven (®Mathis Thermotester). After the interval given, the "yellowness index" (YI) according to ASTM D 1925 is determined on a test specimen. The results are listed in Tables 4a to 4h.

TABLE 4a

| Melamine derivative | YI after exposure time in minutes | | | | |
|---|---|---|---|---|---|
| | 0 | 5 | 10 | 15 | 20 |
| without | 9.2 | 17.6 | 16.8 | 15.7 | 13.8 |
| Compound 2a-A-4 | 4.1 | 5.1 | 5.2 | 5.3 | 6.3 |
| Compound 3a-B-14 | 2.0 | 8.1 | 7.7 | 7.8 | 8.3 |

TABLE 4b

| Melamine derivative | YI after exposure time in minutes | | | | |
|---|---|---|---|---|---|
| | 0 | 5 | 10 | 15 | 20 |
| without | 10.4 | 14.4 | 15.4 | 16.6 | 16.8 |
| Compound 1-A-6 | 5.5 | 6.7 | 6.6 | 7.7 | 9.0 |

TABLE 4c

| Melamine derivative | YI after exposure time in minutes | | | | |
|---|---|---|---|---|---|
| | 0 | 5 | 10 | 15 | 20 |
| without | 9.7 | 12.3 | 14.6 | 16.3 | 17.0 |
| Compound 3a-B-18 | 5.7 | 7.7 | 7.9 | 7.7 | 8.2 |
| Compound 3a-B-19 | 5.5 | 6.5 | 6.5 | 7.0 | 7.4 |
| Compound 3a-B-20 | 5.3 | 6.0 | 6.5 | 7.0 | 7.3 |

TABLE 4d

| Melamine derivative | YI after exposure time in minutes | | | | |
|---|---|---|---|---|---|
| | 0 | 5 | 10 | 15 | 20 |
| without | 9.8 | 12.0 | 13.5 | 15.8 | 17.1 |
| Compound 3a-B-1 | 5.7 | 6.4 | 7.4 | 7.5 | 7.8 |
| Compound 3a-B-2 | 5.4 | 6.5 | 6.7 | 7.0 | 7.3 |
| Compound 3a-B-3 | 5.3 | 7.0 | 7.5 | 7.4 | 7.6 |
| Compound 3a-B-4 | 5.2 | 6.3 | 6.6 | 7.0 | 7.0 |
| Compound 3a-B-5 | 5.6 | 7.3 | 7.3 | 7.6 | 8.3 |

TABLE 4e

| Melamine derivative | YI after exposure time in minutes | | | | |
|---|---|---|---|---|---|
| | 0 | 5 | 10 | 15 | 20 |
| without | 9.0 | 14.8 | 16.7 | 17.4 | 17.1 |
| Compound 3b-B-1 | 3.3 | 4.5 | 5.0 | 5.5 | 6.5 |
| Compound 3b-B-2 | 3.2 | 4.8 | 4.7 | 5.1 | 5.6 |
| Compound 3b-B-3 | 2.9 | 4.4 | 5.0 | 5.2 | 5.8 |
| Compound 3b-B-4 | 3.3 | 3.6 | 4.2 | 4.6 | 5.5 |
| Compound 3b-B-5 | 2.7 | 3.5 | 3.7 | 4.7 | 4.9 |

TABLE 4f

| Melamine derivative | YI after exposure time in minutes | | | | |
|---|---|---|---|---|---|
| | 0 | 5 | 10 | 15 | 20 |
| without | 8.4 | 13.8 | 15.0 | 16.3 | 16.5 |
| Compound 1-A-5 | 3.0 | 4.4 | 4.6 | 4.9 | 5.9 |

TABLE 4g

| Melamine derivative | YI after exposure time in minutes | | | | |
|---|---|---|---|---|---|
| | 0 | 5 | 10 | 15 | 20 |
| without | 8.3 | 13.7 | 15.1 | 17.6 | 17.9 |
| Compound 3a-B-8 | 3.1 | 4.3 | 4.6 | 5.0 | 5.8 |
| Compound 3a-B-10 | 3.0 | 5.1 | 6.0 | 6.1 | 6.3 |
| Compound 3a-B-11 | 4.3 | 5.2 | 5.7 | 6.6 | 7.7 |
| Compound 3b-B-14 | 3.8 | 5.6 | 6.2 | 6.7 | 8.2 |
| Compound 3b-B-15 | 4.3 | 5.7 | 5.9 | 7.1 | 7.6 |

TABLE 4h

| Melamine derivative | YI after exposure time in minutes | | | | |
|---|---|---|---|---|---|
| | 0 | 5 | 10 | 15 | 20 |
| without | 10.7 | 16.4 | 18.3 | 17.9 | 17.9 |
| Compound 3b-B-20 | 3.5 | 4.8 | 5.2 | 5.9 | 6.4 |
| Compound 3b-B-6 | 3.1 | 4.2 | 5.0 | 5.2 | 6.1 |

EXAMPLE 10

A dry mixture comprising 100 parts of PVC (®Solvic 264 GA), 3 parts of epoxidised soya bean oil, 0.35 part of calcium stearate, 0.15 part of zinc stearate, 0.55 part of diisodecylphenyl phosphite, and 0.3 part of the melamine derivative listed in Tables 5a to 5k is rolled on mixing rolls at 180° C. for 5 minutes. Test specimens of the 0.3 mm thick rolled sheet formed are subject to thermal stress at 180° C. in a test oven (®Mathis Thermotester). After the interval given, the "yellowness index" (YI) according to ASTM D 1925 is determined on a test specimen. The results are listed in Tables 5a to 5k.

TABLE 5a

| Melamine derivative | YI after exposure time in minutes | | | | | | |
|---|---|---|---|---|---|---|---|
| | 0 | 5 | 10 | 15 | 20 | 25 | 30 |
| without | 20.1 | 25.1 | 29.9 | 31.8 | 28.1 | 31.6 | 62.8 |
| Compound 2a-A-3 | 2.6 | 4.7 | 4.0 | 6.9 | 10.5 | 18.7 | 35.7 |

TABLE 5b

| Melamine derivative | YI after exposure time in minutes | | | | |
|---|---|---|---|---|---|
| | 0 | 5 | 10 | 15 | 20 |
| without | 19.5 | 27.6 | 30.5 | 33.4 | 30.2 |
| Compound 1-A-8 | 3.4 | 4.9 | 5.9 | 7.6 | 12.8 |

TABLE 5c

| Melamine derivative | YI after exposure time in minutes | | | | |
|---|---|---|---|---|---|
| | 0 | 5 | 10 | 15 | 20 |
| without | 22.4 | 37.4 | 38.5 | 36.9 | 41.2 |
| Compound 3a-B-19 | 2.7 | 7.1 | 10.3 | 14.7 | 24.5 |
| Compound 3a-B-20 | 3.2 | 8.3 | 10.6 | 15.0 | 24.7 |

TABLE 5d

| Melamine derivative | YI after exposure time in minutes | | | | |
|---|---|---|---|---|---|
| | 0 | 5 | 10 | 15 | 20 |
| without | 16.9 | 36.6 | 36.4 | 34.9 | 53.3 |
| Compound 3b-B-5 | 2.5 | 10.4 | 12.8 | 16.6 | 26.6 |

TABLE 5e

| Melamine derivative | YI after exposure time in minutes | | | | |
|---|---|---|---|---|---|
| | 0 | 5 | 10 | 15 | 20 |
| without | 17.5 | 36.2 | 36.8 | 34.5 | 33.3 |
| Compound 3d-B-1 | 1.9 | 4.8 | 6.8 | 10.0 | 15.8 |

TABLE 5f

| Melamine derivative | YI after exposure time in minutes | | | | |
|---|---|---|---|---|---|
| | 0 | 5 | 10 | 15 | 20 |
| without | 18.0 | 38.3 | 38.5 | 34.7 | 37.0 |
| Compound 2c-A-1 | 3.6 | 6.1 | 8.8 | 13.3 | 18.2 |

TABLE 5g

| Melamine derivative | YI after exposure time in minutes | | | | |
|---|---|---|---|---|---|
| | 0 | 5 | 10 | 15 | 20 |
| without | 16.3 | 37.8 | 38.2 | 34.2 | 44.7 |
| Compound 3a-B-12 | 2.8 | 7.0 | 9.4 | 14.0 | 23.7 |

TABLE 5h

| Melamine derivative | YI after exposure time in minutes | | | | |
|---|---|---|---|---|---|
| | 0 | 5 | 10 | 15 | 20 |
| without | 17.5 | 36.3 | 37.4 | 57.2 | 79.0 |
| Compound 2a-A-4 | 3.2 | 9.2 | 11.8 | 16.6 | 21.8 |
| Compound 3a-B-15 | 3.1 | 11.1 | 13.1 | 17.6 | 24.1 |

TABLE 5i

| Melamine derivative | YI after exposure time in minutes | | | | |
|---|---|---|---|---|---|
| | 0 | 5 | 10 | 15 | 20 |
| without | 15.7 | 36.2 | 37.3 | 49.3 | 74.0 |
| Compound 3a-B-13 | 6.2 | 11.4 | 12.6 | 15.6 | 20.6 |

TABLE 5j

| Melamine derivative | YI after exposure time in minutes | | | | |
|---|---|---|---|---|---|
| | 0 | 5 | 10 | 15 | 20 |
| without | 17.0 | 38.4 | 37.5 | 33.8 | 44.5 |
| Compound 3b-B-11 | 2.1 | 6.6 | 8.5 | 10.6 | 12.8 |

TABLE 5k

| Melamine derivative | YI after exposure time in minutes | | | | |
|---|---|---|---|---|---|
| | 0 | 5 | 10 | 15 | 20 |
| without | 15.0 | 32.1 | 37.7 | 36.9 | 31.8 |
| Compound 3b-B-20 | 1.5 | 5.0 | 5.7 | 7.4 | 11.9 |

EXAMPLE 11

A dry mixture comprising 100 parts of S-PVC (®Vinnol H 70 DF), 17 parts of dioctyl phthalate, 3 parts of epoxidised soya bean oil, 0.33 part of zinc oleate, 0.53 part of barium p-(t-butyl)benzoate, 0.7 part of diisodecylphenyl phosphite, 0.44 part of butyldiglycol and 0.2 part of the melamine derivative listed in Table 6 is rolled on mixing rolls at 190° C. for 5 minutes. Test specimens of the 0.3 mm thick rolled sheet formed are subjected to thermal stress at 180° C. in a test oven (®Mathis Thermotester). After the interval given, the "yellowness index" (YI) according to ASTM D 1925 is determined on a test specimen. The results are listed in Table 6.

TABLE 6

| Melamine derivative | YI after exposure time in minutes | | | | | | | | | |
|---|---|---|---|---|---|---|---|---|---|---|
| | 0 | 5 | 10 | 15 | 20 | 25 | 30 | 35 | 40 | 45 |
| without | 9.2 | 11.6 | 13.6 | 15.2 | 18.5 | 18.7 | 17.4 | 15.9 | 14.6 | 15.1 |
| Compound 2a-A-3 | 2.8 | 3.0 | 3.2 | 3.7 | 3.8 | 4.3 | 5.2 | 5.1 | 5.5 | 7.7 |

What is claimed is:

1. A composition comprising
   a) a chlorine-containing polymer,
   b) 0.01 to 0.9% by weight, relative to the chlorine-containing polymer, of a compound of the formula I and/or its hydrochloride,

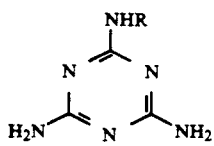 (I)

in which R is $C_7$-$C_{11}$phenylalkyl, $C_7$-$C_{11}$phenylalkyl which is substituted on the phenyl by 1 to 3 radicals, these radicals, independently of one another, being hydroxyl, chlorine, $C_1$-$C_4$alkyl, methoxy or ethoxy, or R is furthermore a group of the formula IIb,

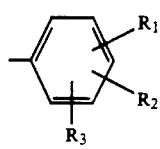 (IIb)

in which $R_1$, $R_2$ and $R_3$, independently of one another, are hydrogen, $C_1$-$C_{20}$alkyl, $C_1$-$C_{20}$alkyloxy, $C_1$-$C_{20}$alkylthio, $C_2$-$C_{12}$alkyloxycarbonyl, $C_2$-$C_{12}$alkanoyl, phenyl, phenyloxy, phenylthio, hydroxyl, mercapto or chlorine, and
   c) 0.01 to 5% by weight, relative to the chlorine-containing polymer, of an Me(II) carboxylate and/or Me(II)-phenolate, in which Me(II) is Ba, Ca, Mg, Cd or Zn.

2. A composition according to claim 1 with the proviso that component c) is a mixture of barium/zinc carboxylates if component b) is phenylmelamine.

3. A composition according to claim 1, in which R is benzyl, benzyl which is substituted on the phenyl by 1 to 3 radicals, these radicals, independently of one another, being hydroxyl, chlorine, $C_1$-$C_4$alkyl, methoxy or ethoxy, or R is furthermore a group of the formula IIb, in which $R_1$, $R_2$ and $R_3$, independently of one another, are hydrogen, $C_1$-$C_{10}$alkyl, $C_1$-$C_{10}$alkyloxy, $C_8$-$C_{18}$alkylthio, $C_2$-$C_{12}$alkyloxycarbonyl, $C_2$-$C_6$alkanoyl, phenyloxy, phenylthio, hydroxyl, mercapto or chlorine.

4. A composition according to claim 1, in which R is benzyl.

5. A composition according to claim 1, in which R is a group of the formula IIb.

6. A composition according to claim 1, in which R is a group of the formula IIb and the radicals $R_1$, $R_2$ and $R_3$, independently of one another, are hydrogen, $C_1$-$C_4$alkyl, $C_1$-$C_4$alkyloxy, $C_8$-$C_{16}$alkylthio, $C_2$-$C_{12}$alkyloxycarbonyl, hydroxyl, mercapto or chlorine.

7. A composition according to claim 1, in which R is a group of the formula IIb, $R_1$ is hydrogen, $R_2$ and $R_3$, independently of one another, are $C_1$-$C_4$alkyl, $C_1$-$C_4$alkyloxy, $C_8$-$C_{16}$alkylthio, $C_2$-$C_{12}$alkyloxycarbonyl, hydroxyl or chlorine, and $R_2$ is additionally hydrogen.

8. A composition according to claim 1, in which R is a group of the formula IIb, $R_1$ and $R_2$ are hydrogen and $R_3$ is $C_1$-$C_4$alkyl, $C_1$-$C_4$alkyloxy, $C_8$-$C_{16}$alkylthio, $C_2$-$C_{12}$alkyloxycarbonyl, hydroxyl or chlorine.

9. A composition according to claim 1, in which component b) is the hydrochloride of a compound of the formula I.

10. A composition according to claim 1, in which component c) is an Me(II) carboxylate, in which Me(II) is Ba, Ca, Mg, Cd or Zn.

11. A composition according to claim 1, in which component c) is a mixture of barium/zinc carboxylates and/or calcium/zinc carboxylates.

12. A composition according to claim 1, in which component a) is polyvinyl chloride.

13. A process for stabilising a chlorine-containing polymer against thermodegradation, which comprises incorporating in the chlorine-containing polymer components b) and c) according to claim 1.

* * * * *